United States Patent [19]

Howard et al.

[11] 4,345,097
[45] Aug. 17, 1982

[54] CHLORINATION OF PHENOLS AND PHENOXYACETIC ACIDS WITH SULFURYL CHLORIDE

[75] Inventors: Kenneth J. Howard, North Little Rock; Albert E. Sidwell, Jacksonville, both of Ark.

[73] Assignee: Vertac Chemical Corporation, Memphis, Tenn.

[21] Appl. No.: 113,724

[22] Filed: Jan. 21, 1980

[51] Int. Cl.³ .................... C07C 39/32; C07C 59/148
[52] U.S. Cl. .................................... 562/472; 568/776
[58] Field of Search ......................... 562/472; 568/776

[56] References Cited

U.S. PATENT DOCUMENTS 4,160,114 7/1979 Shelton .............................. 568/776

OTHER PUBLICATIONS

E. Earl Royals, Advanced Organic Chemistry, p. 454, 1959.

Primary Examiner—Paul J. Killos
Attorney, Agent, or Firm—Hammond & Littell, Weissenberger and Muserlian

[57] ABSTRACT

The process for the chlorination of aromatic compounds of the formula:

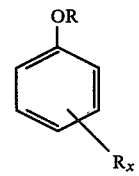

wherein R is a member selected from the group consisting of hydrogen, carboxymethyl, and carboxyethyl and $R_x$ is a member selected from the group consisting of hydrogen, 2-methyl, 2,5-dichloro, and 2-chloro, with the proviso that when R is hydrogen, $R_x$ is 2,5-dichloro, consisting of reacting said aromatic compound with sulfuryl chloride in the presence of elemental sulfur or certain sulfur compounds as a catalyst, optionally together with the presence of a Friedel-Crafts acid catalyst and/or an inert organic solvent at temperatures of from 30° C. to 150° C., and recovering a para chlorinated compound.

9 Claims, No Drawings

CHLORINATION OF PHENOLS AND PHENOXYACETIC ACIDS WITH SULFURYL CHLORIDE

BACKGROUND OF THE INVENTION

This invention relates to the predominantly para chlorination of phenols and phenoxyacetic acid employing sulfuryl chloride in the presence of elemental sulfur or certain other sulfur compounds as a catalyst.

The chlorination of aromatic compounds with sulfuryl chloride is generally known. For example, DuBois in Z. F. Chem. 705 (1866) reported that treatment of molten phenol with an equal molar amount of sulfuryl chloride yields only p-chlorophenol. Sulfuryl chloride was first reported as a chlorinating agent for o-cresol by Sah and Anderson in J. Am. Chem. Soc. 63, 3164 (1941). Their data showed that o-cresol reacted with sulfuryl chloride to yield 84% of the 4-chloro-o-cresol.

Sullivan in U.S. Pat. No. 2,777,002 and British Pat. No. 948,601 reported that phenols, especially those containing hydrogen or an ortho-para direction group in the ortho position, may be converted to the p-halophenol in yields as high as 95% at temperatures not exceeding 75° C. by the use of 1.1 mols of sulfuryl halide per mol of phenol in the presence of 0.5 to 2% of a Friedel-Crafts metallic halide catalyst. Haesler et al in German Pat. No. 1,203,275 further improved the work of Sullivan by finding that if the Friedel-Crafts catalysts was introduced into the reaction as a powdered metal rather than as a salt, the yield of the 4-chloro-o-cresol was increased. Throughout these reactions, the rate of chlorination has been low. For instance, Sullivan shows essentially complete reaction at temperatures of 10° to 30° C. in no less than 8 hours.

The chlorination of benzene with sulfuryl chloride in the presence of a catalyst of sulfur, sulfur chloride and mixtures of AlCl₃ and sulfur chloride is described by Silberrad in J. Chem. Soc., 119, 2029 (1921) and British Pat. No. 193,200. Such chlorinations do not show the selectivity of the present invention.

U.S. Pat. No. 3,920,757 describes the chlorination of phenolic types of aromatic compounds with sulfuryl chloride where the rate of reaction is substantially increased and the selectivity of the reaction toward para chlorination is enhanced by conducting the reaction in the presence of a small but effective amount of certain metal salt-organic sulfur catalysts. Patentee, however, found with his cocatalysts that the temperature was critical and should be maintained below 60° C. where para chlorination was desired.

The presently employed technology to produce 2,4,5-trichlorophenoxyacetic acid (2,4,5-T) and 2,4,5-trichlorophenol (2,4,5-TCP) commercially involves the dechlorination of 1,2,4,5-tetrachlorobenzene with aqueous sodium hydroxide or anhydrous sodium hydroxide in the presence of alcohols under elevated temperatures and pressures to form 2,4,5-TCP according to the reaction:

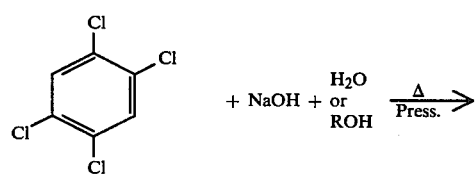

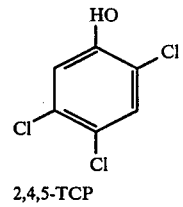

2,4,5-TCP

Under the conditions of alkalinity, temperature and pressure, this process produces between 1 to 100 parts per million of the highly toxic teratogen 2,3,7,8-tetrachlorodibenzo-p-dioxin (TCDD) according to the reaction:

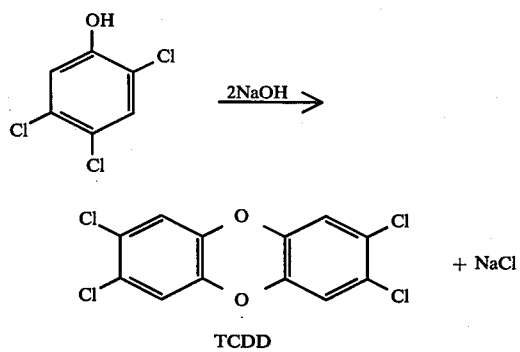

TCDD

In the production of 2,4,5-TCP by this process, the TCDD produced is usually separated by careful distillation, extraction or by adsorption on activated carbon. However, the TCDD is claimed to be extremely toxic and cannot readily be disposed of. TCDD is a highly stable compound which is difficult to destroy chemically. Waste disposal by burying is unsatisfactory. Its destruction by incineration is a possibility which is presently being investigated. However, incineration of such a highly chlorinated compound is difficult and presents the possibility of contamination of either the scrubber liquor, the exhaust gas, or any solid residues.

The production of 2,4,5-T from 2,4,5-TCP is by reaction with monochloroacetic acid according to the reaction:

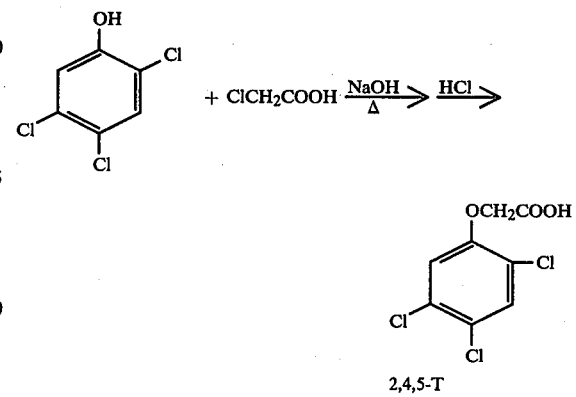

2,4,5-T

Conditions of this reaction are mild in comparison to the hydrolysis step to produce 2,4,5-TCP. Consequently no measurable new formation of TCDD can be observed in the latter reaction.

OBJECTS OF THE INVENTION

An object of the present invention is the development of a process for the production of 2,4,5-trichlorophenol analytically free of 2,3,7,8-tetrachloro-dibenzo-p-dioxin, and its use in the production of 2,4,5-trichlorophenoxyacetic acid.

Another object of the present invention is the development of a process for the chlorination of 2,5-dichlorophenoxyacetic acid selectively and in high yields to give 2,4,5-trichlorophenoxyacetic acid analytically free of 2,3,7,8-tetrachloro-dibenzo-p-dioxin.

A further object of the present invention is the development in the process for the chlorination of aromatic compounds having the formula:

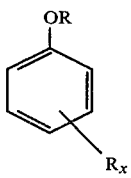

wherein R is a member selected from the group consisting of hydrogen, carboxymethyl, and carboxyethyl and $R_x$ is a member selected from the group consisting of hydrogen, 2-methyl, 2,5-dichloro and 2-chloro, with the proviso that when R is hydrogen, $R_x$ is 2,5-dichloro, consisting of reacting said aromatic compound with sulfuryl chloride, and recovering a para chlorinated compound, the improvement consisting of conducting said reaction with sulfuryl chloride in the presence of elemental sulfur, with or without a like amount of a Friedel-Crafts acid, as a catalyst, and in the presence of from 0 to 500% by weight, based on the amount of said aromatic compound, of an inert organic solvent at a temperature of from 30° C. to 250° C. while passing in said sulfuryl chloride uniformly over an appropriate time period. Such time period may be from 30 minutes to 24 hours.

These and other objects of the invention will become more apparent as the description thereof proceeds.

DESCRIPTION OF THE INVENTION

The present invention relates to a process for the chlorination of aromatic compounds of the formula:

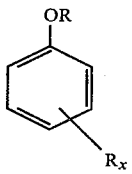

wherein R is a member selected from the group consisting of hydrogen, carboxymethyl and carboxyethyl and $R_x$ is a member selected from the group consisting of hydrogen, 2-methyl, 2,5-dichloro, and 2-chloro, with the proviso that when R is hydrogen, $R_x$ is 2,5-dichloro, consisting of reacting said aromatic compound with sulfuryl chloride in the presence of elemental sulfur as a catalyst, optionally together with a Friedel-Crafts acid catalyst and/or an inert organic solvent at temperatures of from 30° C. to 150° C., and recovering a para chlorinated compound.

More particularly, the present invention relates to an improvement in the process for the chlorination of aromatic compounds having the formula:

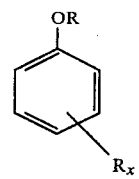

wherein R is a member selected from the group consisting of hydrogen, carboxymethyl, and carboxyethyl and $R_x$ is a member selected from the group consisting of hydrogen, 2-methyl, 2,5-dichloro and 2-chloro, with the proviso that when R is hydrogen, $R_x$ is 2,5-dichloro, consisting of reacting said aromatic compound with sulfuryl chloride, and recovering a para chlorinated compound, the improvement consisting of conducting said reaction with sulfuryl chloride in the presence of elemental sulfur, with or without a like amount of a Friedel-Crafts acid, as a catalyst, and in the presence of from 0 to 500% by weight, based on the amount of said aromatic compound of an inert organic solvent at a temperature of from 30° C. to 150° C. while passing in a stoichiometric amount of said sulfuryl chloride uniformly over a period of from 30 minutes to 24 hours.

Specifically, it has been discovered that by the process of the invention using sulfuryl chloride added slowly to an active sulfur catalyzed solution or melt of:

A. Phenoxyacetic acid, that 98.0–99.0% purity 2,4-dichlorophenoxyacetic acid (2,4-D) can be made at at 98.7% to 99.0% conversion;

B. 2,5-Dichlorophenoxyacetic acid (2,5-D), that 95% to 96% purity of 2,4,5-trichlorophenoxyacetic acid (2,4,5-T), analytically free of 2,3,7,8-tetrachlorodibenzo-p-dioxin (TCDD), can be made at a 98.5% to 99.0% conversion of the available 2,5-D, the remaining 4–5% being composed mainly of 2,4-dichlorophenoxyacetic acid (2,4-D) which was an impurity in the starting 2,5-D;

C. Orthomethylphenoxyacetic acid, that 93% to 95% purity 2-methyl-4-chlorophenoxyacetic acid (MCPA) can be made at 98% to 99% conversion;

D. Orthochlorophenoxyacetic acid (2-CPA), that 97% to 98% purity 2,4-dichlorophenoxyacetic acid (2,4-D) can be made at a 98% to 99% conversion;

E. 2,5-Dichlorophenol (2,5-DCP), that 90% to 92% purity 2,4,5-trichlorophenol (2,4,5-TCP), analytically free of 2,3,7,8-tetrachlorodibenzo-p-dioxin (TCDD), can be made. The remaining 8% to 10% being unreacted 2,5-DCP and other isomers being readily separable by distillation to produce 2,4,5-TCP at a purity of 98.5% to 99.0%.

Crystallization of the resulting phenoxy herbicides from the reaction mass typically results in:

A. or D. 99.5% (or greater) 2,4-D.

B. 99% 2,4,5-T with considerably less than 1% 2,4-D contamination and a mother liquor from which a mixture of 2,4,5-T and 2,4-D can be obtained for sales.

C. 97% MCPA (2-Methyl-4-chlorophenoxyacetic acid).

The sulfur catalyst can be employed in very low quantities of 0.1% by weight or less, based on the amount of the starting aromatic compound. Preferably the catalyst is employed in amounts of from 0.02% to 0.5% by weight, based on the weight of the starting aromatic compound. Optionally a Friedel-Crafts acid may additionally be employed as a catalyst in amounts of from 0 to 0.5% by weight, based on the weight of the starting aromatic compound. The Friedel-Crafts acids are primarily halides or phenates of metals having more than one valency, in the highest valency state, such as halides or phenates of antimony (V), aluminum (III), iron (III), tin (IV), titanium (IV) or zinc (II). In particular, aluminum trichloride or ferric chloride, are employed.

Solvents are not required for the reaction since the aromatic compounds are liquid at some point in the reaction temperature range. However, inert organic solvents may be employed giving a more uniform and even reaction. These inert organic solvents include glacial acetic acid, orthodichlorobenzene, 1,1,2-trichloroethane, nitrobenzene, etc. Many other inert organic solvents having proper solvency for the starting aromatic compounds at the reaction temperatures and sufficient polarity can be employed.

The process of the invention for the production of 2,4-D and MCPA has distinct advantages over the conventional processes in that yields on phenols and chlorine are much higher; no expensive distillation is required; no chlorinated by-products or wastes are formed, and product purity is exceptionally good.

Production of 2,4,5-T is improved by this method by very much higher yields on benzene and chlorine, no by-product methoxydichlorophenol formation during dechlorination of trichlorobenzene, and no formation of tetrachlorodibenzo-p-dioxin (TCDD).

A particularly important aspect of the present invention is the production of 2,4,5-trichlorophenoxyacetic acid analytically free of 2,3,7,8-tetrachlorodibenzo-p-dioxin consisting of, (1) the steps of reacting 2,5-dichlorophenoxyacetic acid with sulfuryl chloride in the presence of sulfur of from 0 to 0.5% by weight as a catalyst, based on the amount of said aromatic compound, with or without added Friedel-Crafts acid, and from 0 to 500% by weight, based on the amount of said aromatic compound of an inert organic solvent at a temperature of from 30° C. to 150° C. while passing in said sulfuryl chloride in stoichiometric amount uniformly over a period of from about 30 minutes to 24 hours, and recovering said 2,4,5-trichlorophenoxyacetic acid analytically free of 2,3,7,8-tetrachlorodibenzo-p-dioxin; and (2) the steps of reacting 2,5-dichlorophenol with sulfuryl chloride in the presence of sulfur of from 0 to 0.5% by weight as a catalyst, based on the amount of said aromatic compound, with or without a Friedel-Crafts acid, and of from 0 to 500% by weight, based on the amount of said aromatic compound of an inert organic solvent at a temperature of from 30° C. to 150° C. while passing in said sulfuryl chloride in stoichiometric amount uniformly over a period of from about 30 minutes to 24 hours, reacting the resultant 2,4,5-trichlorophenol, analytically free of 2,3,7,8-tetrachlorodibenzo-p-dioxin, with chloroacetic acid in the presence of an alkali metal hydroxide at elevated temperatures, acidifying the resultant alkali metal salt and recovering said 2,4,5-trichlorophenoxyacetic acid analytically free of 2,3,7,8-tetrachlorodibenzo-p-dioxin.

Under the present methods of analysis, TCDD can be detected in amounts greater than 2 parts per billion, but analytically free as used in the description of this invention means less than about 100 parts per billion TCDD.

The following examples are illustrative of the practice of the invention without being limitative.

EXAMPLE 1

Production of 2,4,5-T Having No TCDD Contamination

To a 500 ml flask with three necks fitted with a thermometer, condenser, and a dropping funnel, and having a magnetic stirrer, were added 110.5 gms of 95.55% pure 2,5-dichlorophenoxyacetic acid, 50 mls of glacial acetic acid, 10 drops of water, 0.11 gms of finely divided sulfur and 0.11 gms of ferric chloride. This mixture was heated to 50° to 56° C. and 55.5 mls of sulfuryl chloride were added dropwise. An additional 100 mls of acetic acid were added. The reaction mass was slowly heated to 90° C. Upon completion of the reaction, the contents were transferred to a 500 ml beaker with magnetic stirrer and placed in an ice bath. The flask was rinsed into the beaker with two portions of acetic acid of 50 mls each. After cooling to 15° C., the reaction mass was filtered through a Buchner funnel and washed with two 50 ml portions of water. The solid was redissolved in 200 mls of water at 80° C. This solution was cooled to 15° C. and filtered again with a 50 ml water wash. The cake was dried in an oven at 80° C. to a constant weight of 107.5 gms and assayed 98.97% 2,4,5-T with no TCDD detectable at the detection level of 2 ppb.

EXAMPLE 2

Production of 2,4,5-Trichlorophenol Having No TCDD Contamination

To a 500 ml flask fitted as in Example 1 were added 163 gms of 2,5-dichlorophenol, 0.16 gms of finely divided sulfur, and 0.16 gms of ferric chloride at a temperature of 58° C. Sulfuryl chloride amounting to 176 gms was added to the reaction mixture over a 1¾ hour period of time. The temperature was allowed to rise to 95° C. The reaction was held at 70° C. overnight and quenched with 150 mls of water. The aqueous suspension was stirred for one hour at 65° C., and then transferred to a separatory funnel with an additional 150 mls of water used to rinse the reactor. After five to ten minutes of agitation, the layers were allowed to separate and the heavy phenol layer drained to a flask. Three portions of 50 mls of methylene chloride were used to extract residual phenols from the water layer. The methylene chloride extracts were combined with the phenol layer. A total of 197.9 gms of phenols was obtained by vacuum evaporation of the methylene chloride. The composition was 90.2% 2,4,5-TCP, 3.3% unreacted 2,5-DCP, and 6.5% other isomers. Distillation under vacuum followed by coupling with monochloroacetic acid produced a 98.7% 2,4,5-T having no TCDD detectable at a 2 ppb level.

EXAMPLE 3

Production of 2-Methyl-4-Chlorophenoxyacetic Acid

Orthomethylphenoxyacetic acid in the amount of 83.1 gms, 0.04 gms of finely divided sulfur, and 100 gms of glacial acetic acid were added to a 250 ml, three-necked flask fitted with a thermometer, a condenser, and an additional buret. A magnetic stirrer was used for agitation. A total of 81.5 gms of sulfuryl chloride was added slowly over a six-hour period at temperatures of 85° to 95° C. Solvent was removed from the reaction mass by vacuum evaporation yielding 99.2 gms of solids analyzing as 93.5% 2-methyl-4-chlorophenoxyacetic acid which is a 98.8% yield.

EXAMPLE 4

Production of 2,4-Dichlorophenoxyacetic Acid

To a 250 ml flask fitted as in Example 3, were added 38 gms of phenoxyacetic acid, 0.04 gms of finely divided sulfur, and 110.6 gms of nitrobenzene. A total of 76.8 gms of sulfuryl chloride was added over a four-hour period at a temperature of 85° to 95° C., which was maintained for an additional two hours. The reactor and contents were then slowly cooled to 10° C. and centrifuged to remove the crystals from the liquor.

The crystals were washed with 10 gms of cold octane and dried. A total of 45.2 gms of dry crystals having an assay of 99.6% 2,4-dichlorophenoxyacetic acid were collected.

The filtrate liquor from the first batch was placed back in the reactor along with a fresh charge of 30.4 gms of phenoxyacetic acid. Sulfuryl chloride amounting to 61.4 gms was again added slowly over a four-hour period at 85° to 95° C. This procedure was repeated to make a total of five reactions conducted in the original solvent.

A total of 159.6 gms of phenoxyacetic acid and 328.9 gms of sulfuryl chloride were consumed in the five consecutive reactions. The amount of crystalline 2,4-dichlorophenoxyacetic acid (2,4-D) collected was 211.1 gms for a 92.8% recovery. An additional amount of 2,4-D remaining in the final filtrate of 13.6 gms would add another 6.0% to the recovery figure for a total percent of theory of 98.8%. All batches of crystalline product analyzed greater than 99% 2,4-D.

EXAMPLE 5

Production of 2,4-Dichlorophenoxyacetic Acid 76.0 gms of phenoxyacetic acid and 0.04 gm of finely divided sulfur were added to a three-necked, 100 ml flask with a magnetic stirring bar. The flask was fitted with a water-cooled condenser, a thermometer, a heating mantle, and a buret. Sulfuryl chloride was added slowly over a 16-hour period at temperatures ranging from 95° to 152° C.

The resulting reaction mass including samples for analytical purposes accounted for 99.37% of theoretical yield, and had an assay of 98.28% 2,4-D.

EXAMPLE 6

Production of 2,4,5-T Having No TCDD Contamination

Using the apparatus of Example 5, 110.5 gms of technical 2,5-D acid, 0.05 gm of finely divided sulfur, and 150 gms of nitrobenzene were added to the flask. Sulfuryl chloride was added slowly over a six-hour period at temperatures of 90° to 100° C. Analysis of the reaction mass indicated 94.5% 2,4,5-T, 3.8% (2,4-D and 2,5-D), 0.9% 2,4,6-T and related isomers. Crystallization of the reaction mass yielded 110.2 gms of 99.2% 2,4,5-T acid.

This method for 2,4,5-T acid production has the further advantage that no 2,3,7,8-tetrachlorodibenzo-p-dioxin (TCDD) is produced during the dechlorination step which produces 2,5-dichlorophenol. No trace of TCDD could be detected to less than 2 ppb in the 2,4,5-T produced by this method.

The preceding examples are illustrative of the practice of the invention. It is to be understood, however, that other expedients known to those skilled in the art or disclosed herein, may be employed without departing from the spirit of the invention or the scope of the appended claims.

We claim:

1. In the process for the chlorination of aromatic compounds having the formula:

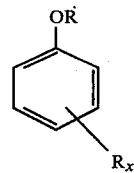

wherein R is a member selected from the group consisting of hydrogen, carboxymethyl, and carboxyethyl and $R_x$ is a member selected from the group consisting of hydrogen, 2-methyl, 2,5-dichloro and 2-chloro, with the proviso that when R is hydrogen, $R_x$ is 2,5-dichloro, consisting of reacting said aromatic compound with sulfuryl chloride, and recovering a para chlorinated compound, the improvement consisting of conducting said reaction with sulfuryl chloride in the presence of elemental sulfur, with or without a like amount of a Friedel-Crafts acid, as a catalyst, and, optionally, an inert organic solvent at a temperature of from 30° C. to 250° C. while passing in a stoichiometric amount of said sulfuryl chloride uniformly over a period of about 30 minutes to 24 hours.

2. The process of claim 1 wherein said elemental sulfur catalyst is present in an amount of from 0.02% to 0.5% by weight, based on the weight of the starting aromatic compound.

3. The process of claims 1 or 2 wherein R is hydrogen, $R_x$ is 2,5-dichloro and no solvent is employed.

4. The process of claims 1 or 2 wherein R is carboxymethyl and $R_x$ is 2,5-dichloro.

5. The process of claims 1 or 2 wherein R is carboxymethyl and $R_x$ is hydrogen.

6. The process of claims 1 or 2 wherein R is carboxymethyl and $R_x$ is 2-methyl.

7. The production of 2,4,5-trichlorophenoxyacetic acid analytically free of 2,3,7,8-tetrachlorodibenzo-p-dioxin consisting of the steps of reacting 2,5-dichlorophenoxyacetic acid with sulfuryl chloride in the presence of elemental sulfur, with or without a like amount of a Friedel-Crafts acid, as a catalyst, and in the presence of from 0 to 500% by weight, based on the amount of said aromatic compound of an inert organic solvent at a temperature of from 30° C. to 150° C. while passing in a stoichiometric amount of said sulfuryl chloride uniformly over a period of from 30 minutes to 24 hours, and recovering said 2,4,5-trichlorophenoxyacetic acid analytically free of 2,3,7,8-tetrachlorodibenzo-p-dioxin.

8. The process of claim 7 conducted in the presence of an inert organic solvent selected from the group consisting of acetic acid and nitrobenzene.

9. The production of 2,4,5-trichlorophenoxyacetic acid analytically free of 2,3,7,8-tetrachlorodibenzo-p-dioxin consisting of the steps of reacting 2,5-dichlorophenol with sulfuryl chloride in the presence of elemental sulfur as a catalyst, of from 0 to 0.5% by weight, based on the amount of said aromatic compound, of a Friedel-Crafts acid, and of from 0 to 500% by weight, based on the amount of said aromatic compound of an inert organic solvent at temperature of from 30° C. to 150° C. while passing in a stoichiometric amount of said sulfuryl chloride uniformly over a period of from 30 minutes to 24 hours, reacting the resultant 2,4,5-trichlorophenol analytically free of 2,3,7,8-tetrachlorodibenzo-p-dioxin with chloroacetic acid in the presence of an alkali metal hydroxide at elevated temperatures, acidifying the resultant alkali metal salt and recovering said 2,4,5-trichlorophenoxyacetic acid analytically free of 2,3,7,8-tetrachlorodibenzo-p-dioxin.

* * * * *